United States Patent [19]

Brandley et al.

[11] Patent Number: 5,094,740

[45] Date of Patent: * Mar. 10, 1992

[54] TWO-DIMENSIONAL ELECTROPHORETIC SEPARATION OF CARBOHYDRATES

[75] Inventors: Brian K. Brandley; Robert J. Stack, both of Alameda, Calif.

[73] Assignee: Glycomed, Inc., Alameda, Calif.

[*] Notice: The portion of the term of this patent subsequent to Dec. 4, 2007 has been disclaimed.

[21] Appl. No.: 591,360

[22] Filed: Sep. 27, 1990

Related U.S. Application Data

[63] Continuation-in-part of Ser. No. 481,361, Feb. 16, 1990, Pat. No. 4,975,165.

[51] Int. Cl.$^5$ ............................................. G01N 27/26
[52] U.S. Cl. .............................. 204/182.1; 204/182.8; 204/299 R; 536/127
[58] Field of Search ............... 204/180.1, 182.1, 182.8, 204/299 R; 536/127

[56] References Cited

U.S. PATENT DOCUMENTS

| | | | |
|---|---|---|---|
| 4,109,075 | 8/1978 | Deaton | 536/1 |
| 4,305,799 | 12/1981 | Schwartz et al. | 204/299 R |
| 4,666,581 | 5/1987 | Itoh et al. | 204/299 R |
| 4,975,165 | 12/1990 | Brandley et al. | 204/299 R |

Primary Examiner—John Niebling
Assistant Examiner—David G. Ryser
Attorney, Agent, or Firm—Morrison & Foerster

[57] ABSTRACT

Separation methodology is disclosed which allows for the separation of mixtures of carbohydrates into highly resolved detectable bands of carbohydrates. The method involves first reacting a mixture of carbohydrates with charge generating moieties which are capable of fluorescing such as 1-amino-4-naphthalene sulfonic acid (ANSA) to form carbohydrate conjugates. The conjugates are subjected to a first-dimensional gel electrophoresis in a first direction to provide separate bands of carbohydrates in the gel. A band in the gel is removed and subjected to second-dimensional electrophoresis in a second direction which is substantially perpendicular to the first direction. More specific bands of more highly resolved carbohydrates are then formed in the second-dimensional gel. The more specific bands within the second-dimensional gel are then electro-blotted onto a substrate surface and can be viewed in extremely small amounts due to the fluorescent capability of the ANSA when viewed under ultraviolet light.

24 Claims, No Drawings ial zones. These zones can be examined and studied by applications of standard electrophoretic practice such as fixing, staining and washing to remove buffers. Desirably, the electrophoretic media is a thin gel film coated on a suitable support, commonly glass or plastic. Such an arrangement permits the electrophoretic separation to be achieved in a minimum of time with a maximum degree of resolution.

TWO-DIMENSIONAL ELECTROPHORETIC SEPARATION OF CARBOHYDRATES

CROSS-REFERENCE

This application is a continuation-in-part of our pending, U.S. application Ser. No. 07/481,361, filed Feb. 16, 1990 U.S. Pat. No. 4,975,165, which application is incorporated herein by reference and to which application we claim priority under 35 U.S.C. § 120. Further, this application is related in part to two other co-pending U.S. applications filed concurrently with the present application on Sept. 27, 1990. One related application is entitled "Fluorescent Tag for Sugar Electrophoresis" invented by Brian K. Brandley and Robert J. Stack, the co-inventors of the present invention, and Michael Tiemeyer; the other application is entitled "Electro-Blotting of Electro-phoretically Resolved Fluorescent-Labeled Saccharides and Detection of Active Structures With Protein Probes" invented by Brian K. Brandley, Paul G. James, Michael Tiemeyer and Robert J. Stack, all of whom are inventors working in the same research organization as the present inventors with an obligation to assign the invention to the same entity. The above-referenced applications are each incorporated herein by reference in their entireties.

FIELD OF THE INVENTION

This invention relates generally to methods of separating various carbohydrates utilizing electrophoresis and electro-blotting techniques. More particularly, the invention relates to a two-dimensional electrophoresis procedure wherein saccharides are attached to charged molecules (which fluoresce on exposure to ultraviolet light) and separated first in one dimension and then in a second dimension followed by electro-blotting to obtain highly resolved groups of separated carbohydrates.

BACKGROUND OF THE INVENTION

Electrophoresis is a well known technique for the separation of a charged species by utilizing their differences in rate of migration under the influence of an electrical field. The procedure has proved invaluable for the resolution and isolation of complex biological substances such as enzymes, serums, carbohydrates, proteins, DNA and RNA. Most analytical electrophoresis methods are based on zone-electrophoresis in which a thin zone of a sample material is applied to the electrophoretic medium. The electrophoretic migration of the sample components results in the formation of fractional zones. These zones can be examined and studied by applications of standard electrophoretic practice such as fixing, staining and washing to remove buffers. Desirably, the electrophoretic media is a thin gel film coated on a suitable support, commonly glass or plastic. Such an arrangement permits the electrophoretic separation to be achieved in a minimum of time with a maximum degree of resolution.

Various hydrophilic colloids, for example, starch, agarose and cellulose derivatives have been used in forming electrophoretic gel films, but polyacrylamide is preferred. One reason for preferring polyacrylamide is that gels can be prepared from it having a wide range of pore size. This is accomplished primarily by varying the ratio of acrylamide polymer to the N, N', methylenebisacrylamide cross-linking reagent.

The resulting polyacrylamide gels provide high resolution electrophoretic separation of important biopolymers, for example, proteins and nucleic acids. In addition, the absence of ionized groups in polyacrylamide gels render such gels suitable as an anticonvection medium for isoelectric focusing.

Once the electrophoretic techniques have been applied in order to separate the materials in the gel, it is necessary to transfer the separated materials from the gel to a support where they can be tested. A number of procedures are available for transferring the electrophoretically resolved materials from the gel. One such procedure involves electro-blotting. This type of transfer procedure involves transferring the resolved bands within the gel to a support matrix such as a nitrocellulose sheet. The transfer is carried out by the application of an electric field and therefore is distinguishable from a more conventional alternative which involves the capillary transfer of such materials usually used in techniques such as southern and northern blotting.

SUMMARY OF THE INVENTION

A method of separating carbohydrates such as saccharides using two-dimensional electrophoresis is disclosed. The method involves reacting a mixture of carbohydrates with a suitable charge generating moiety capable of fluorescing such as 1-amino-4-naphthalene sulfonic acid (ANSA) to form conjugates in the form of charged carbohydrate conjugates capable of fluorescing. The conjugates are subjected to a first-dimensional gel electrophoresis in a first direction for a sufficient period of time to form separate bands of conjugates in the electrophoresis gel. A separated band of conjugates is removed from the gel. The separated band is then subjected to a second-dimensional gel electrophoresis in a second direction wherein the second direction is substantially perpendicular to the first direction. The second-dimensional gel electrophoresis is carried out for a sufficient period of time to form separate bands of conjugates in the second-dimensional electrophoresis gel. Accordingly, highly resolved groups of saccharides (in conjugate forms) are obtained which can be electro-blotted to a substrate and tested for their affinity to labeled probes.

A primary object of the invention is to provide an improved method for separating carbohydrates such as saccharides utilizing two-dimensional gel electrophoresis.

An advantage of the present invention is that by utilizing two-dimensional gel electrophoresis more specific refinement regarding the separation of different carbohydrates can be obtained.

A feature of the present invention is that carbohydrates bound to charged molecules are first separated using gel electrophoresis in one direction to obtain separated groups which groups are then separated by gel electrophoresis in a second direction substantially perpendicular to the first direction.

Another object of the present invention is to provide a means for testing the affinity of particular carbohydrates to labeled probes.

Another advantage of the present invention is that the charged molecules (e.g., ANSA) which are bound to the carbohydrates provide a charge and also act as fluorescent labels when subjected to ultraviolet light.

Another feature of the present invention is that the first electrophoretic gel is a borate-containing acrylamide gel whereas the second electrophoresis gel is a glycine-containing acrylamide gel and the two types of gels provide different types of separation thus providing the best separation features of both types of gels and a high degree of resolution of the carbohydrates subjected to such two-dimensional electrophoresis methodology.

These and other objects, advantages and features of the present invention will become apparent to those persons skilled in the art upon reading the details of the structure, synthesis and usage as more fully set forth below, reference being made to the accompanying general structural formulae forming a part hereof.

DETAILED DESCRIPTION OF PREFERRED EMBODIMENTS

Before the present method for separating and testing carbohydrates is described, it is to be understood that this invention is not limited to the particular carbohydrates, saccharides, proteins or process steps described as such compounds and steps may, of course, vary. It is also to be understood that the terminology used herein is for the purpose of describing particular embodiments only and is not intended to be limiting since the scope of the present invention will be limited only by the appended claims.

It must be noted that as used in the specification and the appended claims, the singular forms "a", "an" and "the" include plural referents unless the context clearly dictates otherwise. Thus, for example, reference to "a carbohydrate" includes mixtures of carbohydrates, reference to "an oligosaccharide" or saccharide includes reference to mixtures of saccharides, and reference to "the electrophoretic processing step" includes a variety of similar steps of the type described herein.

The first step of the present invention involves binding the mixtures of carbohydrate molecules to be tested to a charged molecule capable of fluorescing. The charged moiety must be attached in order to allow for the carbohydrate materials to be separated from each other by electrophoretic techniques which apply a charge differential in a field and thus require that the materials being separated have electrical charges thereon. In connection with the present invention, the carbohydrates (preferably saccharides) are conjugated with one or more suitable moieties such as 1-amino-4-naphthalene sulfonic acid (hereinafter ANSA). Although the carbohydrate must be conjugated to a moiety which provides a charge and must be conjugated to a moiety which is capable of fluorescing, they may be two separate moieties, i.e., the carbohydrate may bond to a charge generating moiety (which is not fluorescent) and then bound to a fluorescent moiety which is not charged. Further, the charge generating moiety and fluorescent moiety may each be bound directly to the carbohydrate or may be bound to each other with either moiety then being bound to the carbohydrate.

The two-dimensional separation techniques of the invention can be used to separate a wide range of carbohydrates, but is particularly useful with respect to the separation of saccharides. More particularly, the invention has unique advantages with respect to separating smaller saccharides such as monosaccharides, disaccharides and trisaccharides. Throughout this disclosure, the terms "carbohydrate" and "saccharide" are at times used interchangeable in that the particular structure of the compound being separated is not part of the present invention and the present invention can be used to separate all types of carbohydrates. However, it is pointed out that closely related compounds, such as closely related saccharides are more difficult to separate by conventional electrophoresis methods, thus making the present invention particularly useful with respect to separating closely related saccharides.

As indicated above, the invention first involves the preparation of a conjugate which is a bi-functional conjugate formed by binding the carbohydrates (mixtures to be separated) to a bi-functional moiety. Although such moieties are generally useful if they (a) provide a charge, and (b) are capable of fluorescing, preferred moieties are characterized by having (1) a primary amine (which can react with and bind to a saccharide), (2) one or more charged groups (which allow movement in a charged field such as that provided in electrophoresis separation), (3) a fluorescent moiety (allowing bands of separated carbohydrates to be visualized under ultra violet light), and (4) a 228 relatively small molecular weight, e.g., less than 500, preferably 200 to 300 (so as to not interfere with the electrophoretic separation techniques due to the size of the moiety being attached to the carbohydrate.

Some moieties which are capable of fluorescing, but which do not provide a charge include naphthalene, fluorescein, aminonaphthalene and aminofluorescein. Some moieties which do not fluoresce but are capable of providing a charge upon ionization include various sulfates and carbonates.

Examples of bi-functional moieties capable of providing a charge and of fluorescing include:
1-amino-4-(2-hydroxyethyl)piperazine;
2-amine-9-hydroxyfluorene;
2-amino-6-hydroxy-8-mercaptopurine;
4-amino-6-hydroxy-2-mercaptopyrimidine monohydrate;
2-amino-4-hydroxy-6-methylpyrimidine;
4-amino-3-hydroxy-1-naphthalenesulfonic acid;
4-amino-6-hydroxy-1-naphthalenesulfonic acid;
6-amino-4-hydroxy-2-naphthalenesulfonic acid monohydrate;
7-amino-4-hydroxy-2-naphthalenesulfonic acid monohydrate;
3-amino-5-hydroxypyrazole;
$\propto$ 4-amino-6-hydroxypyrazolo[3,4-d]pyrimidine;
4-amino-1-naphthalenecarbonitrila;
3-amino-2,7-naphthalenedisulfonic acid, monosodium salt;
7-amino-1,3-naphthalenedisulfonic acid, monopotassium salt;
2-amino-1-naphthalenesulfonic acid;
4-amino-1-naphthalenesulfonic acid;
5-amino-2-naphthalenesulfonic acid;
8-amino-2-naphthalenesulfonic acid;
4-amino-1,8-naphthalic anhydride;
4-amino-1,8-naphthalimide;
3-amino-2-naphthoic acid;
4-amino-1,2-naphthoquinone hemihydrate;
6-aminonicotinamide;
5-((2-aminoethyl)amino)naphthalene-1-sulfonic acid, sodium salt; and
N-(2-aminoethyl)-4-amino-3,6-disulfo-1,8-naphthalene, dipotassium salt.

Any salts of the above-listed acids or acids of the above-listed salts can also be used in connection with the present invention. Further, other derivatives of these compounds may also be useful as will apparent to those skilled in the art upon reading the present disclosure.

In connection with a preferred embodiment, one or more ANSA moieties are bound to the carbohydrate.

The 1-amino-4-naphthalene sulfonic acid (ANSA) preferably used in connection with the present invention has the following structure:

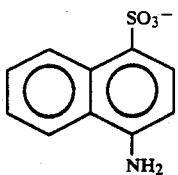

The —NH₂ amino group is indicated as being at the "1" position and the —SO₃⁻ group is at the "4" position. The shared double bonds in each ring structure provide the fluorescent character to the ANSA when the ANSA is exposed to ultraviolet light. It is pointed out that it is possible to add more —SO₃⁻ groups to the rings to increase the charge but such is not preferred in connection with the present 2-D separation methods.

One preferred class of charge-generating moieties capable of fluorescing can be more generally described by the following general structural formula:

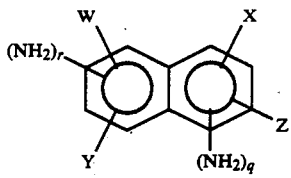

wherein each of W, X, Y and Z are independently hydrogen or an ionizable, charge-generating moieties such as $-SO_3^-$ or $-CO_2^-$, and q and r are independently 0 or 1 with the proviso that one of r or q is 1.

It is preferable if only one of W, X, Y and Z is an ionizable charged-generating moiety and the others are each hydrogen and the ionizable charged-generating moiety is preferably a sulfonate. Further, it should be pointed out that alpha-amino naphthalene sulfonic acids are most preferably used in connection with the present invention and are more preferable than beta-amino naphthalene sulfonic acids.

After the bi-functional carbohydrate conjugates are formed, i.e., bound to charged and fluorescing moieties, the conjugates are subjected to electrophoretic techniques in order to resolve the different carbohydrates from each other. The electrophoretic resolution provides a gel wherein the carbohydrates are separated from each other in different bands along the length of the gel.

In accordance with the present invention, the first-dimensional or first step gel electrophoresis process is carried out with what is referred to as a "borate-containing gel" or "boric acid-containing acrylamide gel". A specific example of such a gel includes 40% acrylamide, 5% bis gel (in 40 mM Tris, 40 mM boric acid, 1 mM EDTA, pH 8.5). Such a gel and methods of preparing such are described in Example 1. As used in connection with the present invention, a "borate-containing gel" shall include all gels of the type described within Example 1 and such gels which obtain a separation of small carbohydrates and saccharides in substantially the same manner described within Example 1.

As used in connection within this invention, the term "glycine containing gel" shall be distinguishable from a "borate containing gel". The "glycine containing gels" are of the type described within Example 1 in the "second-dimension" gel electrophoresis process. Such gels capable of separating carbohydrates and specifically smaller saccharides in the same manner as described within example 1 in the "second-dimension" gel electrophoresis process are to be encompassed by the term "glycine containing gels".

The separation techniques used in connection with this invention are particularly advantageous when used with smaller carbohydrate compounds. More specifically, the two-dimensional gel electrophoresis process of the invention works particularly well in resolving monosaccharides, disaccharides and trisaccharides of closely related types. Conventional procedures are generally not capable of providing sufficient resolution to separate away such smaller saccharides into distinct bands. The addition of a group such as the ANSA group provides a sufficient amount of charge to allow for the separation of the smaller saccharides into distinct groups but does not apply too much charge so that the charge quality overwhelms any characteristic of the saccharide and does not provide for resolution among different types of closely related saccharides. Further, the shared double bonds within the ring structure of the fluorescing moiety such as naphthalene or, more specifically, ANSA provide for the fluorescent capability of the conjugates formed. Accordingly, when different bands of saccharides are separated away from each other, it is possible to visually view these bands simply by the application of ultraviolet light this provides a significant advantage in that any given band can be removed and manipulated or tested as desired.

It is important to point out that conventional techniques require the presence of approximately 10 micromoles of a substance in order to have a detectable band of that substance appear within an electrophoresis gel. However, when utilizing the procedures of the present invention, it is possible to detect a fluorescent band of the compound if the compound is present in as small amounts as 1 to 5 picomoles.

The use of the fluorescent tag provides a number of advantages over and above the use of other tags. For example, the fluorescent is substantially safer and less expensive than the use of a radiolabel. Further, the use of a fluorescent tag is substantially less cumbersome and more efficient than the use of antibody-linked enzyme tags. These advantages are obtained concurrently with the overall advantage of providing a tag which allows for greatly improved resolution especially as used in connection with smaller saccharide compounds.

The carbohydrates within the different resolved bands are then transferred to a nylon membrane by electro-blotting techniques. The electro-blotting procedures transfer the carbohydrates in the gel to the nylon membrane and the carbohydrates become bound to the nylon membrane thus providing a stable record of the electrophoretic separation of the carbohydrates within the gel.

After the first-dimensional and second-dimensional gel electrophoresis processes are carried out, the fluorescent bands of conjugates present within the gels must be transferred to a membrane surface. A number of different types of membrane surfaces can be utilized in connection with the invention. However, nylon is preferable. The transfer of the carbohydrate conjugates from the gel to the surface of the substrate is carried out by utilizing electro-blotting techniques. The electro-blotting is carried out for a sufficient period of time to allow substantial amounts of the conjugates (preferably all of the conjugates) within the gel to transfer to and bind to the surface of the substrate thus providing a permanent record of the separated bands of conjugated on the surface of the membrane.

The electro-blotting procedures which can be used in connection with the present invention are procedures generally known to those skilled in the art. In general, a gel having the separated conjugates thereon is placed in contact with a membrane surface. The membrane surface which is preferably a charged nylon surface is preferably first wetted with a buffer in which the electro-blotting procedure will be carried out. What is arbitrarily chosen as the cathode side of the gel (i.e., ultimately towards the negative electrode when positioned in the electro-blotting tank) is placed in contact with the surface of the nylon substrate after the substrate has been moistened with the electro-blotting buffer. Any air bubbles between the gel and the nylon membrane should be removed by gently pushing the nylon substrate against the gel using powder-free gloved fingers. A piece of nitrocellulose can be placed on the opposite side of the gel and all of the air bubbles should be removed between the gel and the nitrocellulose. Such a construct is then placed in the electro-blotting tank which contains a buffer solution and has an anode and a cathode therein. The power supply is then turned on and the charge differential created by the power supply will draw the electrically charged carbohydrate conjugates out of the gel and onto the charged surface of the nylon substrate. The transfer time is dependent somewhat on the thickness of the gel and the size of the conjugates being transferred to the nylon substrate. The transfer can be monitored by viewing the transfer under ultraviolet light to ensure complete transfer of all the materials to the nylon substrate. Overnight transfer is reliable and convenient.

One of the surprising discoveries of the present invention is that the specific bands of conjugates in the gel are even more clearly resolved and distinguishable from each other when the transfer is made to the nylon substrate surface. While not wishing to be bound to any particular theory, it is believed that greater resolution is obtained on the nylon surface because the light is not diffused as it is when the fluorescent light is emanating from the gels when exposed to ultraviolet light. Regardless of the reason, it has been found that distinct bands of conjugates are formed on the nylon substrate surface. Further, this electro-blotting procedure onto the nylon substrates is what makes possible the detection of the extremely small amounts of material within the bands, e.g., 1 to 5 picomoles of a carbohydrate.

It is possible to increase the ability to detect small amounts of carbohydrate by binding moieties which fluoresce, but which do not impart additional charge, e.g., naphthalene. The inclusion of large additional charge would overwhelm the separation procedure to the extent that other characteristics of the saccharide would not be born out when separating closely related smaller sacharrides.

The carbohydrates on the nylon membrane can then be tested for their ability to bind particular labeled probes such as labeled proteins, i.e., tested for potential carbohydrate-protein affinity. The carbohydrate/-protein affinity is tested by first preparing a mixture of proteins and attaching the proteins to suitable labels of the type known to those skilled in the art. It should be pointed out that radio-labeled proteins are particularly preferred.

The two-dimensional separation techniques of the present invention can be utilized in order to test a variety of different types of compounds for their affinity to a variety of different types of carbohydrates bound to the nylon substrate surface. For example, the invention can be utilized to test the affinity of certain lectins for their affinity to certain carbohydrates. Particular types of antireceptor proteins known to be positioned on viruses and to be attachable to certain carbohydrates on cell surfaces can be tested. Further, the affinity of certain growth factor proteins to particular carbohydrates bound on the substrate surface can be assayed. It is believed that the attachment of certain carbohydrates to growth factor proteins can effect the activity of the growth factor proteins in vivo.

The molecules to be tested, such as the protein molecules to be tested for their affinity to certain carbohydrates, must, of course, be bound to a label which is later detectable. A variety of different types of labels known to those skilled in the art can, of course, be used. For example, it is possible to utilize radiolabels which are later detected by the use of autoradiography. It is also possible to attach the protein molecules to an antibody which is itself bound to an enzyme such as horseradish peroxidase which can be detected by the addition of reagents which cause a color change. Procedures for attaching the labels to the proteins or other molecules to be assayed are well known to those skilled in the art and are described within the literature.

The labeled proteins are brought into contact with the nylon membranes having the highly resolved bands of carbohydrates thereon. The proteins are allowed to remain in contact with the carbohydrates for sufficient amounts of time under conditions which would allow for binding if binding is to occur. Thereafter, the membranes are washed to remove any unbound protein material. After the washing, the nylon membranes are subjected to detection procedures in order to determine if and where proteins have bound to the carbohydrates on the nylon membrane. The carbohydrates which bind proteins are of particular interest for further study. For example, such carbohydrates may be useful in acting as false receptors to virus antireceptors and thus provide for a means for blocking viral infections.

The following example is provided so as to give those of ordinary skill in the art a complete disclosure and description of how to carry out the carbohydrate separation processes of the invention and are not intended to limit the scope of what the inventor regards as his invention. Efforts have been made to ensure accuracy with respect to numbers used (e.g., amounts, temperature, etc.) but some experimental errors and deviation should be accounted for. Unless indicated otherwise, parts or parts by weight, temperature is in degrees centigrade, and pressure is at or near atmospheric.

EXAMPLE 1

Mixtures of monosaccharides and oligosaccharides with a free reducing end are reacted with 1-amino-4-naphthalene sulfonic acid (ANSA) to form a mixture of conjugates. Reaction buffer is 0.15 M NaOAc, pH 5.0. ANSA is added at a 20–100 fold molar excess and the reaction incubated at 55° C. for 1 hour. Sodium cyanoborohydride is then added equimolar to the ANSA, and the reaction incubated at 55° C. overnight in the dark.

The reaction mix is dried under $N_2$, brought up in distilled water with 10% glycenol.

ELECTROPHORESIS

1. First Dimension. A (0.75mm width) 40% acrylamide/5% bis gel (in 40mM Tris, 40mM boric acid, 1mM EDTA, pH 8.5) was pored with a 5% acrylamide/minigel 5% bis stacking gel. The running buffer (upper and lower) was Tris/borate as above. The monosaccharide reaction mix was loaded, and run at 500 volts for about 2 hours, in an ice bath. Sugar bands were visible in U.V. light (365 nm) and a 5mm wide band from one lane excised.

2. Second Dimension. A 1.0mm wide 40% acrylamide gel/5% bis in 0.375M Tris/HCl(pH 8.8) was poured in a Biorad minigel apparatus. A stacking gel of 5% acryl/5% bis in 0.1225M Tris/HCl pH 6.0 was added. The excised first-dimension gel was lain on the stacking gel and secured with 1% agarose. The gel was run in Tris/glycine (25mM) pH 8.3 at 300 volts for 1 hour then 500 volts until the phenol red tracking dye neared the end of the gel. The gels were removed and sugar spots detected by U.V. This procedure separates saccharides such as glucose, galactose, mannose, glcNAc, glucuronic acid, galacturonic acid, iduronic acid, as well as a variety of charged disaccharides.

The instant invention is shown and described herein in what is considered to be the most practical, and preferred embodiments. It is recognized, however, that departures may be made therefrom which are in the scope of the invention and that obvious modifications will occur to one skilled in the art upon reading this disclosure.

What is claimed is:

1. A method of separating a mixture of carbohydrates using two-dimensional electrophoresis, comprising the steps of:
   reacting the mixture of carbohydrates with charge generating moieties and moieties capable of fluorescing to form carbohydrate conjugates;
   subjecting the carbohydrate conjugate to a first-dimensional gel electrophoresis in a first direction for a sufficient period of time to form separate bands of conjugates in the electrophoresis gel;
   removing a band of conjugates from the gel; and
   subjecting the removed band of conjugates to a second-dimensional gel electrophoresis in a second direction, which is substantially perpendicular to the first direction, for a sufficient period of time to form separate bands of conjugates in the second-dimensional electrophoresis gel.

2. The method as claimed in claim 1, wherein the charge generating moieties and moieties capable of fluorescing are the same moieties which are a charge generating moieties capable of fluorescing.

3. The method as claimed in claim 2, wherein the charge generating moieties capable of fluorescing are selected from the group consisting of:
   1-amino-4-(2-hydroxyethyl)piperazine;
   2-amine-9-hydroxyfluorene;
   2-amino-6-hydroxy-8-mercaptopurine;
   4-amino-6-hydroxy-2-mercaptopyrimidine monohydrate;
   2-amino-4-hydroxy-6-methylpyrimidine;
   4-amino-3-hydroxy-1-naphthalenesulfonic acid;
   4-amino-6-hydroxy-1-naphthalenesulfonic acid;
   6-amino-4-hydroxy-2-naphthalenesulfonic acid monohydrate;
   7-amino-4-hydroxy-2-naphthalenesulfonic acid monohydrate;
   3-amino-5-hydroxypyrazole;
   4-amino-6-hydroxypyrazolo[3,4-d]pyrimidine;
   4-amino-1-naphthalenecarbonitrila;
   3-amino-2,7-naphthalenedisulfonic acid, monosodium salt;
   7-amino-1,3-naphthalenedisulfonic acid, monopotassium salt;
   2-amino-1-naphthalenesulfonic acid;
   4-amino-1-naphthalenesulfonic acid;
   5-amino-2-naphthalenesulfonic acid;
   8-amino-2-naphthalenesulfonic acid;
   4-amino-1,8-naphthalic anhydride;
   4-amino-1,8-naphthalimide;
   3-amino-2-naphthoic acid;
   4-amino-1,2-naphthoquinone hemihydrate;
   6-aminonicotinamide;
   5((2-aminoethyl)amino)napthalene-1-sulfonic acid, sodium salt; and
   N-(2-aminoethyl)-4-amino-3,6-disulfo-1,8-naphthalene, dipotassium salt.
   and any salts of the acids and acids of the salts.

4. The method as claimed in claim 2, wherein the charge generating moieties capable of fluorescing are selected from the group consisting of monosulfonic and disulfonic acid derivatives of amino naphthalene.

5. The method as claimed in claim 1, wherein the charge generating moieties are selected from the group consisting of sulfonates and carbonates.

6. The method as claimed in claim 1, wherein the moieties capable of fluorescing are selected from the group consisting of: naphthalene, fluorescein, aminonaphthalene and amino-fluorescein.

7. The method as claimed in claim 1, further comprising:
   electro-blotting the separate bands of conjugates in the second-dimensional electrophoresis gel from the gel onto the surface of a membrane.

8. The method as claimed in claim 7, further comprising:
   contacting the substrate surface with labeled probes to determine the affinity of the probes to bind to carbohydrates on the surface.

9. The method as claimed in claim 8, further comprising:
   washing away any labeled probes not bound to a carbohydrate and detecting bound probes by their label.

10. A method as claimed in claim 7, wherein individual bands on the membrane surface contain less than 10 picomoles of carbohydrate and further wherein said bands can be observed when the substrate surface is viewed in ultraviolet light.

11. The method as claimed in claim 10, wherein the carbohydrates are present in the bands in an amount of 1 to 5 picomoles.

12. The method as claimed in claim 1, wherein the first-dimensional gel is a borate-containing gel.

13. The method as claimed in claim 1, wherein the second-dimensional gel is a glycine-containing gel.

14. The method as claimed in claim 1, wherein the mixture of carbohydrates includes monosaccharides.

15. The method as claimed in claim 1, wherein the mixture of carbohydrates includes disaccharides.

16. The method as claimed 1, wherein the mixture of carbohydrates includes trisaccharides.

17. A method for assaying for the affinity of a protein for a carbohydrate in a mixture of carbohydrates, comprising the steps of:

reacting the mixture of carbohydrates with charge generating moieties and moieties capable of fluorescing to form carbohydrate conjugates;

subjecting the carbohydrate conjugates to first-dimensional gel electrophoresis in a first direction for a sufficient period of time to form separate bands of conjugates in the electrophoresis gel;

removing a band of conjugates from the gel;

subjecting the removed band of conjugates to a second-dimensional gel electrophoresis in a second direction, which is substantially perpendicular to the first direction, for a sufficient period of time to form separate bands of conjugates in the second-dimensional electrophoresis gel;

electro-blotting the separate bands of conjugates in the second-dimensional electrophoresis gel onto the surface of a membrane; and contacting the membrane having the conjugates thereon with labeled probes to determine the affinity of the probes to bind to carbohydrates on the membrane.

18. The method as claimed in claim 17, wherein the charge generating moieties and moieties capable of fluorescing are the same moieties which are a charge generating moieties capable of fluorescing.

19. The method as claimed in claim 17, wherein the carbohydrates on the substrate surface are present in at least one band in an amount in the range of 1 to 5 picoliters and further wherein the band containing 1 to 5 picoliters of carbohydrates is visibly observable with the naked eye under ultraviolet light.

20. A membrane the surface of which has bound thereto a plurality of bands of carbohydrate material which carbohydrate material is bound to 1-amino-4-naphthalene sulfonic acid and which bands are observable with the naked eye when the bands are viewed under ultraviolet light.

21. The membrane as claimed in claim 20, wherein at least one band on the surface which is observable with the naked eye under U.V. light contains from about 1 to about 5 picomoles of carbohydrate.

22. A bi-functional conjugate in the form of a carbohydrate bound to a charge-generating moiety capable of fluorescing having the following general structural formula:

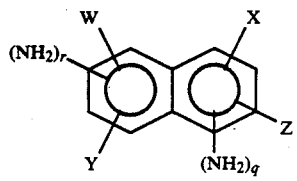

wherein each of W, X, Y and Z are independently hydrogen or an ionizable charge-generating moiety selected from the group consisting of $-SO_3-$, $-CO_2-$ and q and r are each independently 0 or 1 with the proviso that one of r or q is 1.

23. The conjugate as claimed in claim 22, wherein only one of W, X, Y and Z is an ionizable charge-generating moiety and one of q or r is 0.

24. The conjugate as claimed in claim 23, wherein the charge-generating moiety is a sulfonate.

* * * * *